(12) United States Patent
Majeed et al.

(10) Patent No.: US 7,300,682 B2
(45) Date of Patent: Nov. 27, 2007

(54) METHOD OF PREPARATION AND USE OF COCONUT WATER IN MAMALIAN TISSUE NOURISHMENT GROWTH AND HEALTHY MAINTENANCE

(75) Inventors: Muhammed Majeed, Piscataway, NJ (US); Vladimir Badmaev, Piscataway, NJ (US)

(73) Assignees: Sabinsa Corporation, Piscataway, NJ (US); Sami Labs Ltd., Bangalore (IN)

( * ) Notice: Subject to any disclaimer, the term of this patent is extended or adjusted under 35 U.S.C. 154(b) by 530 days.

(21) Appl. No.: 10/416,017

(22) PCT Filed: Nov. 15, 2001

(86) PCT No.: PCT/US01/42948

§ 371 (c)(1),
(2), (4) Date: Nov. 3, 2003

(87) PCT Pub. No.: WO02/40043

PCT Pub. Date: May 23, 2002

(65) Prior Publication Data

US 2004/0067264 A1    Apr. 8, 2004

Related U.S. Application Data

(60) Provisional application No. 60/248,223, filed on Nov. 15, 2000.

(51) Int. Cl.
*A23L 1/212*    (2006.01)
*A01N 65/00*    (2006.01)

(52) U.S. Cl. ............. 426/617; 424/727; 424/776
(58) Field of Classification Search .......... 424/727; 426/617
See application file for complete search history.

(56) References Cited

U.S. PATENT DOCUMENTS

| 2,736,645 A | 2/1956 | Steward et al. |
| 5,654,255 A | 8/1997 | O'Neal et al. |
| 5,891,440 A | 4/1999 | Lansky |

FOREIGN PATENT DOCUMENTS

| CN | 1057161 A | * | 12/1991 |
| GB | 2318969 A |   | 5/1998 |
| JP | 07322849 A | * | 12/1995 |

OTHER PUBLICATIONS

PTO 2007-2523; Translation of CN 1057161 A, "Perennial Preservation Method for Coconut Endosperm", Translated by: Linguist System, Inc.*
English language abstract of CN 1,057,161, Dec. 25, 1991.

* cited by examiner

*Primary Examiner*—Michele Flood
(74) *Attorney, Agent, or Firm*—Arent Fox LLP

(57) ABSTRACT

A nutritional, cosmetic and pharmaceutical compositions containing active ingredients from the liquid endosperm of fresh green coconuts, and a method for obtaining the active ingredients.

13 Claims, No Drawings

METHOD OF PREPARATION AND USE OF COCONUT WATER IN MAMALIAN TISSUE NOURISHMENT GROWTH AND HEALTHY MAINTENANCE

This application claims priority to provisional application No. 60/248,223 filed on Nov. 15, 2000.

FIELD OF THE INVENTION

The invention relates to nutritional, cosmetic and pharmaceutical compositions containing active ingredients from fresh green coconuts, and methods for obtaining the compositions.

BACKGROUND OF THE INVENTION

Coconut water is the liquid endosperm of *Cocos nucifera* L an is used as a supplement in media for the growth of plant tissue cultures. The coconut fruit is unique in that it accumulates large amounts of this liquid over periods of a year or more in its life cycle. The greatest amount of coconut water is found in young, green coconuts and provides nourishment for the growth of the solid endosperm (coconut meat) inside the hard shell of the fruit. When the fruit matures, both the solid endosperm and the remaining coconut water serve as nutrients for the developing embryo and seedling. Thus coconut water serves as a natural reservoir of nutrients to promote tissue growth[1].

The nutritional composition of coconut water obtained from fruits at different stages of maturity has been determined. The medium is rich in proteins, amino acid sugars, vitamins, minerals and growth hormones (Table 1) essential to the promotion of tissue growth. In addition, shikimic acids and quinic acids have been detected in samples of coconut water from fruits at different stages of maturity, with the maximum amounts being found in young green coconuts. The probable role of these alicyclic acids in romatic biosynthesis, indicates their importance in the developing coconut. They may also play a significant role in the nutrition of plant and tissue cultures.

TABLE 1

VITAMIN, GROWTH FACTOR, SUGAR ALCOHOL AND MINERAL CONTENT OF COCONUT WATER

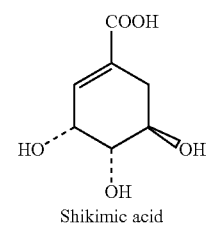

Shikimic acid

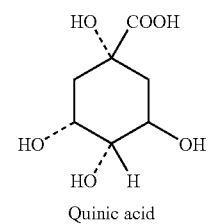

Quinic acid

| COMPOUND | Mg/L |
| --- | --- |
| Nicotinic acid | 0.64 |
| Pantothenic acid | 0.52 |
| Biotin | 0.02 |
| Riboflavin | 0.01 |
| Folic acid | 0.003 |
| Thiamine | Trace |
| Pyridoxime | Trace |
| Auxin | 0.07 |
| Gibberellin | * |
| 1,3-Diphenylurea | 5.8 |
| Sorbitol | 15.0 |
| M-inositol | 0.01 |
| Scyllo-inositol | 0.05 |

| | Mg/100 g |
| --- | --- |
| Potassium | 312.0 |
| Chloride | 183.0 |
| Sodium | 105.0 |
| Phosphorous | 37.0 |
| Magnesium | 30.0 |
| Sulfur | 24.0 |
| Iron | 0.10 |
| Copper | 0.04 |

* A significant growth response was obtained from dwarf peas with an extract of 188 ml of coconut water.

The RNA-phosphorus (RNA-P) content of coconut water was found to be consistently high at all levels of fruit maturity (Table 2). The ratio of RNA-P/DNA-P was unusually high. The role of RNA in amino acid transport and respiratory metabolism of living cells is well known. The RNA of coconut water would therefore effectively carry out these and other functions as part of the metabolic machinery essential to the developing endosperm tissue of the coconut and therefore support the growth of other living cells as well, in tissue culture media.

TABLE 2

RNA-PHOSPHORUS AND DNA-PHOSPHORUS OF THE ALCOHOL-INSOLUBLE RESIDUE FROM COCONUT WATER

| | µG/mg alcohol-insoluble residue | | Ratio |
| --- | --- | --- | --- |
| Age of coconuts | RNA-P | DNA-P | RNA-P/DNA-P |
| Young green | 20.05 | 0.06 | 342.5 |
| Mature, green | 32.82 | 2.45 | 13.9 |

Cytokinins are a class of plant growth substances (plant hormones) active in promoting cell division. They are also involved in cell growth and differentiation and in other physiological processes. A major cytokinin found in coconut milk was isolated using a standard procedure, the tobacco callus growth-promoting assay. The structure was determined to be a complex trans-zeatin riboside (G3A2-ZR). The authors of this study attributed at least 20% of the cytokinin activity in coconut milk to this compound[2].

A study that explored the efficacy of single and combined growth regulator treatments of indole-3-acetic acid (IAA), gibberelic acid (GA3) and coconut milk on plant height, yield, chlorophyll and vitamin contents of plants such as *Abelmoschus esculetus* L and *Solanum gilo* L, found that 100 mg/L GA3 and 15% coconut water were significantly effective treatments[3].

The nutritive properties of coconut water are well recognized in Oriental tradition. Immature coconuts are used as a glucose-electrolyte oral re-hydration solution for treatment of diarrhea[4]. Coconut water solids also provide a nutritive medium for beneficial microflora in the gastrointestinal tract. A recent report also mentions the successful use of coconut water as a short-term intravenous hydration fluid[5]. Coconut water has been used traditionally as a nutritional beverage. The FAO was recently granted a patent in the UK for the manufacture of bottled coconut water that retained all nutrients. This is the first patent given to a UN agency. Unlike existing methods their process did not use HTST pasteurization, wherein heat treatment would inactivate some of the biological activity of the coconut water.

Other researchers have obtained an extract from coconut water and milk called Cocogro, a natural product comprised of plant growth hormones and regulators, which enhances the growth of vegetables, legumes fruit trees, cereal crops, flowering plants, etc.

Green coconut milk is reported to be an effective culture medium for animal cells (Rev Bras Biol. 1970(Apr) 30:1: 97-100) and Plasmodium (Trans. R. Soc. Trop. Med Hyg. 1989 83:5, 720). A major cytokinin, G3A2-ZR, was also identified in coconut milk (Kobayashi, H: et al. Experentia, 1995 51:11 1081-84).

Although coconut milk has been used traditionally on the skin as a nourishing agent, green coconut water provides unique nutrients for sustaining cell growth. For example, a protein fraction isolated from coconut water was absent in the milk (Birosel, DM et al. Rev. Farm Bioquim Univ Sao Paulo 1976 14:35-42).

Coconut milk is used in a facemask in U.S. Pat. No. 5,660,840 and in a plant growth regulating composition in U.S. Pat. No. 5654255.

Coconut water was found to be safe for topical use. In laboratory studies, the material is shown to have no irritating effects on the skin, and the $LD_{50}$ value must be greater than 2000 mg/kg when administered through the skin. Accordingly, coconut water is nontoxic.

Coconut water is described as an isotonic sports drink. The comparative properties of coconut water and conventional sports drinks are listed in Table 3[7]:

TABLE 3

SPORTS DRINKS VS. COCONUT WATER

| Component | Sports drinks (mg/100 ml) | Coconut water (mg/100 ml) |
| --- | --- | --- |
| Potassium | 11.7 | 294 |
| Sodium | 41 | 25 |
| Chloride | 39 | 118 |
| Magnesium | 7 | 10 |
| Sugars | 6 | 5 |

DETAILED DESCRIPTION OF THE INVENTION

An object of the invention relates to compositions containing as active ingredients, components obtained from coconut water. The compositions are specifically formulated for use in tissue culture media, more preferably, in supporting or culturing cells and mammalian tissues derived from ectoderm, mesoderm and endoderm.

The composition may be used in topical applications, for example, skin and hair care formulations. The composition may also be formulated into a nutritional supplement so as to be administered by ingestion or intravenously, thereby providing essential nutrients and repair material for the tissues.

The active ingredients of coconut water can be obtained by freeze-drying, and this simple method yields a unique and stable composition with optimum biological activity.

The inventive composition contains optimal amounts of growth hormones (cytokinins) and RNA-phosphorus (RNA-P), an optimal ratio of RNA-P/DNA-P, as well as desired concentrations of shikimic, quinic and indole-3-acetic acids. The inventive composition of the invention differs unexpectedly from that found in raw coconut water, and a list of its components is presented in Table 4.

TABLE 4

Composition of the invention

| Substance | Range |
| --- | --- |
| Total protein | 0.9-1.2% |
| Carbohydrates | 75-85% |
| Sodium | 350-500 mg/100 g |
| Potassium | 3000-4000 mg/100 |
| Magnesium | 200-300 mg/100 g |
| Cytokinins | 0.01-0.03 mg/g |
| Indole-3-acetic acid | 0.005-0.01 mg/g |
| Shikimic/quinic acids | 25-30 Meq/mg |
| RNA-P content | 25-30 μg/g alcohol-insoluble residue |
| RNA-P/DNA-P ratio | 300:1-400:1 |

The RNA-P/DNA-P ratio is 300:1 to 400:1. This is based on literature reports wherein the RNA-P of 20.05 mcg/g was associated with DNA-P 0.06 mcg/g of the alcohol-insoluble residue. RNA-P/DNA-P was therefore approximately 340:1.

Another object of the invention is a unique process for preserving the natural growth promoting properties of green coconut water. The nutritional properties of green coconut water are optimized by a lyophilization process yielding a microbiologically stable preparation that retains the biological activity of the ingredients. Available as a powder, the material of the invention can be conveniently stored and transported for commercial applications. The process ensures that the biological activity of the heat sensitive growth hormones is retained, and that the RNA phosphorus/DNA-phosphorus ratio and the amino acid composition are optimized for maximum biological activity.

The process employs a lyophilization technique, which preserves the biological activity of the active ingredients. The liquid endosperm, obtained from fresh green coconuts at their peak level of maturity, is frozen at −20° C. to −70° C. using a mixture of solid carbon dioxide-acetone, followed by lyophilization in a customized lyophilizer at a reduced pressure of 0.1 to 0.8 mm Hg and a temperature of 35° C. to 40° C. to produce a lyophilized amorphous material. The amorphous nature of the freeze dried material protects the protein components during pulverization and storage. During storage, the material transforms into the more stable crystalline state which is also less hygroscopic. The amorphous material is pulverized under low temperature conditions to yield a powder.

The shikimic and quinic acids content and their activity in the dried powder provide unexpected advantages over the fresh material. The shikimic acid pathway is reported to produce salicylic acid, a known growth promoter in plants. In other systems, shikimic acid and quinic acid function as potent antioxidants. Indole-3-acetic acid (plant auxin), the activity of which is retained in the dried product, has been shown to protect mammalian cells (sperm cells).

The product can be used in topical and cosmetic formulations to promote cell growth such as in skin care and hair care formulations as well as in dry blends for nutritional and sports beverages. The invention is also useful as an inhibitor of tumor cell proliferation in mammalian cells.

REFERENCES

1. Tulecke, W. et al. (1961) The biochemical composition of coconut water (coconut milk)** as related to its use in plant tissue culture. *Contributions from Boyce Thompson Institute*, 21:115-128.
2. Kobayashi, H. et al. (1995) Identification of a major cytokinin in coconut milk. *Experentia* 51(11):1081-1084.
3. Kadiri, M. et al. (1 997) Responses of some Nigerian vegetables of plant growth. *Rev. Biol Trop*. 44-45:23-28.
4. Adams, W. and Bratt, D E. (1992) Young coconut water for home rehydration in children with mild gastroenteritis. *Trop. Geogr. Med*. 44:149-53.
5. Campbell-Falck, D. et al. (2000) The intravenous use of coconut water. *Am J. Emerg. Med* 18(1):108-11.
6. Research Report #6719 and 6720. Indian Institute of Toxicology. May 2000. FAO: *Agriculture*21, New sports drink: coconut water. October 1998.
7. Ma Y, Xu Q P, Sun J N, Bai L M, Guo Y J, Niu J Z Antagonistic effects of shikimic acid against focal cerebral ischemia injury in rats subjected to middle cerebral artery thrombosis. *Chung Kuo Yao Li Hsueh Pao* 1999 Aug.;20(8):701-4
8. Aghil O, Bibby M C, Carrington S J, Double J, Douglas K T, Phillips R M, Shing T K Synthesis and cytotoxicity of shikimate analogues. Structure:activity studies based on 1-crotonyloxymethyl-3R,4R,5R-trihydroxy-cyclohex-2-enone. *Anticancer Drug Des* 1992 Feb.;7 (1):67-82
9. Jones R S, Ali M, Ioannides C, Styles J A, Ashby J, Sulej J, Parke D V The mutagenic and cell transforming properties of shikimic acid and some of its bacterial and mammalian metabolites. *Toxicol Lett* 1983 Oct.-Nov.; 19(1-2):43-50
10. Toniolli R, Bussiere J, Courot M, Magistrini M, Combarnous Y Effect of indole-3-acetic acid (plant auxin) on the preservation at 15 degrees C. of boar semen for artificial insemination. *Reprod Nutr Dev* 1996;36(5):503-11
11. Nalini N, Sabitha K, Chitra S, Viswanathan P, Menon V P Histopathological and lipid changes in experimental colon cancer: effect of coconut kernel (Cocos nucifera Linn.) and (Capsicum annum Linn.) red chili powder. *Indian J Exp Biol* 1997 September;35(9):964-71.

What is claimed:

1. A lyophilized, nutritional composition from liquid endosperm of fresh green coconuts (*Cocos nucifera* L.) comprising proteins, carbohydrates, cytokinins, ribonucleic acid-phosphorus (RNA-P), deoxyribonucleic acid-phosporous (DNA-P), indole-3-acetic acid, shikimic acid and quinic acid.

2. The composition of claim 1, wherein the RNA-P and the DNA-P are at a ratio in a range of 300:1 to 400:1.

3. The composition of claim 1, wherein the shikimic acid is at a concentration range of 25-30 Meq/mg.

4. The composition of claim 1, wherein the quinic acid is at a concentration range of 25-30 Meq/mg.

5. The composition of claim 1, wherein the cytokinins are at a concentration range of 0.01-0.03 mg/g.

6. The composition of claim 1, wherein the indole-3-acetic acid is at a concentration range of 0.005-0.01 mg/g.

7. The composition of claim 1, wherein the composition is a powder.

8. A cosmetic formulation comprising a composition of claim 1.

9. A nutritional supplement for a beverage comprising a composition of claim 1.

10. A process for obtaining a biologically active powder from fresh green coconuts (*Cocos nucifera* L.) comprising the steps of:

a) providing liquid endosperm from coconuts;
b) freezing the liquid endosperm using a mixture of carbon dioxide and acetone to obtain a frozen liquid endosperm;
c) lyophilizing the frozen liquid endosperm of step b) to produce an amorphous material; and
d) pulverizing the amorphous material of step c) to obtain the biologically active powder.

11. The process of claim 10, wherein the liquid endosperm is frozen at a temperature range of from at −20° C. to −70° C.

12. The process of claim 10, wherein the lyophilizing of step c) occurs at a pressure of from 0.1 to 0.8 mm Hg and a temperature of from 35° C. to 40° C.

13. The process of claim 10, wherein the biologically active powder comprises proteins, carbohydrates, cytokinins, RNA-phosphorus (RNA-P), DNA-phosporous (DNA-P), indole-3-acetic acid, shikimic acid and quinic acid.

* * * * *